(12) United States Patent
Ruffolo et al.

(10) Patent No.: US 6,236,807 B1
(45) Date of Patent: May 22, 2001

(54) WICK-BASED LIQUID EMANATION SYSTEM WITH CHILD-RESISTANT AND MINIATURIZATION FEATURES

(75) Inventors: Richard R. Ruffolo, Columbus, OH (US); Anthony Zembrodt, Covington, KY (US); Roberto Zaraboza, New York, NY (US)

(73) Assignee: Bath & Body Works, Inc., Reynoldsburg, OH (US)

( * ) Notice: Subject to any disclaimer, the term of this patent is extended or adjusted under 35 U.S.C. 154(b) by 0 days.

(21) Appl. No.: 09/479,637

(22) Filed: Jan. 7, 2000

(51) Int. Cl.[7] .............................. A61M 16/00; F24F 6/08
(52) U.S. Cl. .......................... 392/390; 392/392; 392/395
(58) Field of Search ..................................... 392/386, 390, 392/392, 394, 395; 261/139, 142, 99, DIG. 65

(56) References Cited

U.S. PATENT DOCUMENTS

| | | |
|---|---|---|
| 1,944,821 | 1/1934 | Blaise . |
| 2,176,345 * | 10/1939 | Hurwitt ................................. 43/131 |
| 4,621,768 | 11/1986 | Lhoste et al. . |
| 4,663,315 * | 5/1987 | Hasegawa et al. ................. 424/76.3 |
| 4,968,487 * | 11/1990 | Yamamoto et al. ................. 422/125 |
| 5,038,394 * | 8/1991 | Hasagawa et al. ................. 392/395 |
| 5,222,186 * | 6/1993 | Schimanski et al. ................ 392/395 |
| 5,290,546 | 3/1994 | Hasegawa et al. . |
| 5,647,053 | 7/1997 | Schroeder et al. . |
| 5,909,845 | 6/1999 | Greatbatch et al. . |

* cited by examiner

Primary Examiner—Sang Paik
(74) Attorney, Agent, or Firm—Colucci & Umans; Peter C. Michalos; Angelo Notaro

(57) ABSTRACT

A vapor emanation system includes a plastic housing having a socket portion and an electric plug portion. A decorative miniaturize container containing liquid to be evaporated by heat, has a body for storing the liquid and a neck connected to the body for engaging the socket portion of the housing for supporting the container on the housing. The neck has a passage there through and a retaining ring is fixed in the passage. A hole extends through the ring. A wick having an upper portion extending through the hole of the retaining ring also has a lower portion extending down into the body of the container for absorbing liquid from the container and for moving the liquid into the upper portion of the wick by capillary action. A tangential electric heater in the housing heats the upper portion of the wick above the neck to evaporate liquid from the wick. A retaining pin extending through the wick below the neck, extends radially beyond the wick by an amount which precludes upward extraction of the wick from the retaining ring to prevent a child from removing the wick and being exposed to the liquid.

19 Claims, 4 Drawing Sheets

WICK-BASED LIQUID EMANATION SYSTEM WITH CHILD-RESISTANT AND MINIATURIZATION FEATURES

FIELD AND BACKGROUND OF THE INVENTION

A present invention relates in general to electric evaporation systems which use wicks, and in particular to a new and useful wick evaporation system having a child-resistant wick retaining structure, a reverse thread feature, unique decorative features and a compact structure.

Wick-based vapor emanation systems are known in the art for dispersing into the air vapors of any number of liquids. Such systems are often used in the home with liquids varying from insect repellent to air freshener. Typically, in such systems, one end of a wick is partially submerged in the liquid to be dispersed. The liquid is contained in any suitable container. The partially submerged portion of the wick absorbs the liquid, some of which diffuses by capillary or wicking action into the exposed, unsubmerged portion of the wick. The exposed portion of the wick is locally heated, often by means of a ring-shaped heater which fits over the wick. This causes the liquid which has diffused into the exposed portion of the wick to evaporate into the surrounding air. Continual application of heat to the exposed portion of the wick results in an evaporation/absorption process that continues until the liquid is consumed.

A problem with conventional wick-based liquid emanation systems, as with many products suitable for home use, is the potential that a child will come into contact with the liquid contents of the system. Many of the liquids utilized with such systems can be harmful if swallowed, and some are harmful if merely touched. Therefore, it is desirable to make these systems "child-resistant " to reduce the chance that a child will access the potentially harmful contents of the system.

U.S. Pat. No. 5,909,845 to Greatbatch, et al. discloses a child-resistant, wick-based liquid emanation system that includes a container which is capable of containing liquid and has an opening. A wick is partially disposed within the container and extends through the opening of the container. A hollow overcap encases the extended portion of the wick and has a closed, separable tip and an open base attached to cover the opening of the container. The system is activated by separating the tip from the overcap. This system is complex and adds a step before the product can be used.

U.S. Pat. Nos. 5,038,394 and 5,290,546 to Hasegawa, et al. disclose an electric air freshener that includes an electric plug which is integral with the vaporizer housing. This structure is common to similar electric evaporators that have been available in Europe and Asia for many years. The housing includes a ring heater for engaging the upper end of a wick for heating that end and vaporizing liquid from a bottle which is screwed into a socket formed as part of the housing.

A similar structure is disclosed in U.S. Pat. No. 5,222,186 to Schimanski, et al. where a tangential heater rather than an ring heater is used as the heating means for heating the upper end of the wick. U.S. Pat. No. 5,222,186 to Schimanski, et al. is incorporated here by reference for its teaching of this type of electric evaporator.

U.S. Pat. No. 5,647,053 to Schroeder, et al. shows a similar structure which can swivel around its plug.

The concept of a wick-based electric evaporator is quite old as demonstrated by U.S. Pat. No. 1,944,821, issued in 1934, and including the same basic units of a wick with an upper end that is heated to vaporize liquid from a container extending below the heater.

SUMMARY OF THE INVENTION

An object of the present invention is to provide a vapor emanation system that includes a plastic housing having a socket portion and an electric plug portion, with safety, decorative and miniaturization features. A decorative container containing liquid to be evaporated by heat, has a body for storing the liquid and a neck connected to the body for engaging the socket portion of the housing for supporting the container on the housing. The neck has a passage there through and a retaining ring is fixed in the passage. A hole extends through the ring. A wick having an upper portion extending through the hole of the retaining ring also has a lower portion extending down into the body of the container for absorbing liquid from the container and for moving the liquid into the upper portion of the wick by capillary action. A tangential electric heater in the housing heats the upper portion of the wick above the neck to evaporate liquid from the wick. A retaining pin extending through the wick below the neck, extends radially beyond the wick by an amount which precludes upward extraction of the wick from the retaining ring to prevent a child from removing the wick and being exposed to the liquid.

The socket and the container are made with reverse screw threads to minimize misuse of the product. With reverse threads, common bottles cannot be used with the system. This prevents a consumer from trying to use volatile and flammable colognes or make-shift wicks in the system which would be dangerous. A typical bottle cannot be attached to the housing of the invention.

Furthermore the use of one or more pins in the wick prevents the wick from being pulled out to allow a consumer to pour in an inappropriate blend of perfumes which are not intended for the system. If the wick cannot be removed the container cannot be refilled by the consumer.

According to another object of the invention, the body of the container may simulate a decorative item such as a bunch of fruit and a vapor dispersing flange above the heater may also be used to further simulate the item, for example by simulated foliage at the top of the fruit.

A still further object of the invention is achieved by miniaturizing the system. To this end the heater is a tangential heater and the socket portion of the housing is smaller in diameter that the largest diameter of the container or bottle body which extends below the housing. The container body is fully visible below the housing, not being covered by any part of the housing.

The various features of novelty which characterize the invention are pointed out with particularity in the claims annexed to, and forming a part of, this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 2:
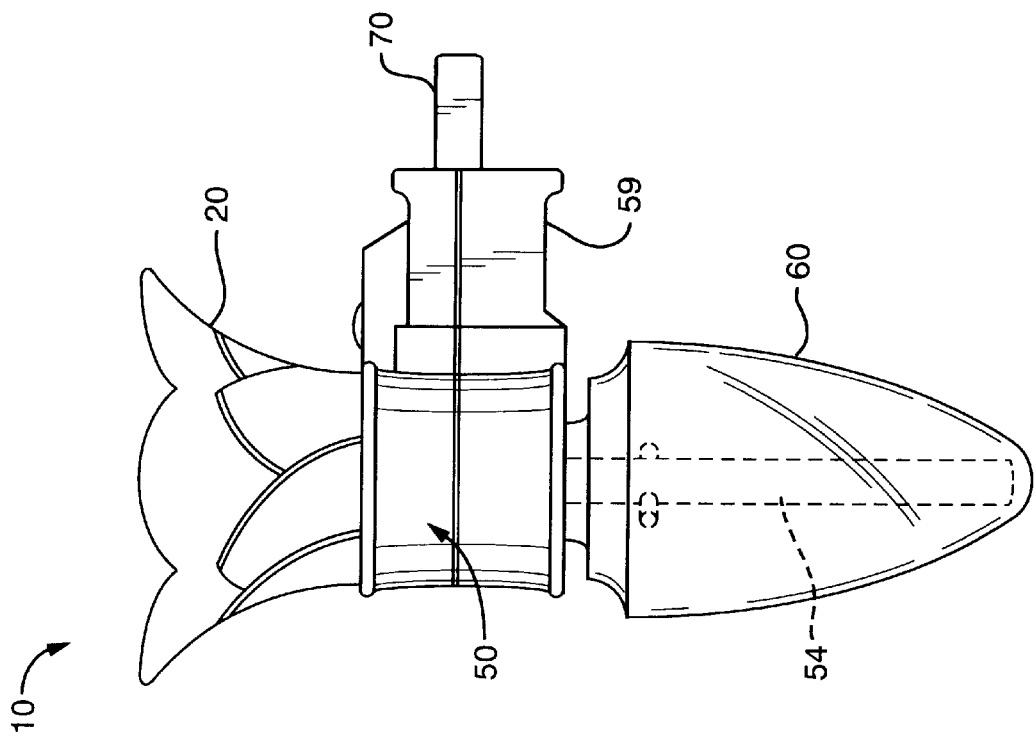
FIG. 2 is a side elevational view of the system including container, housing, retaining and decorative features.
Figure 4:
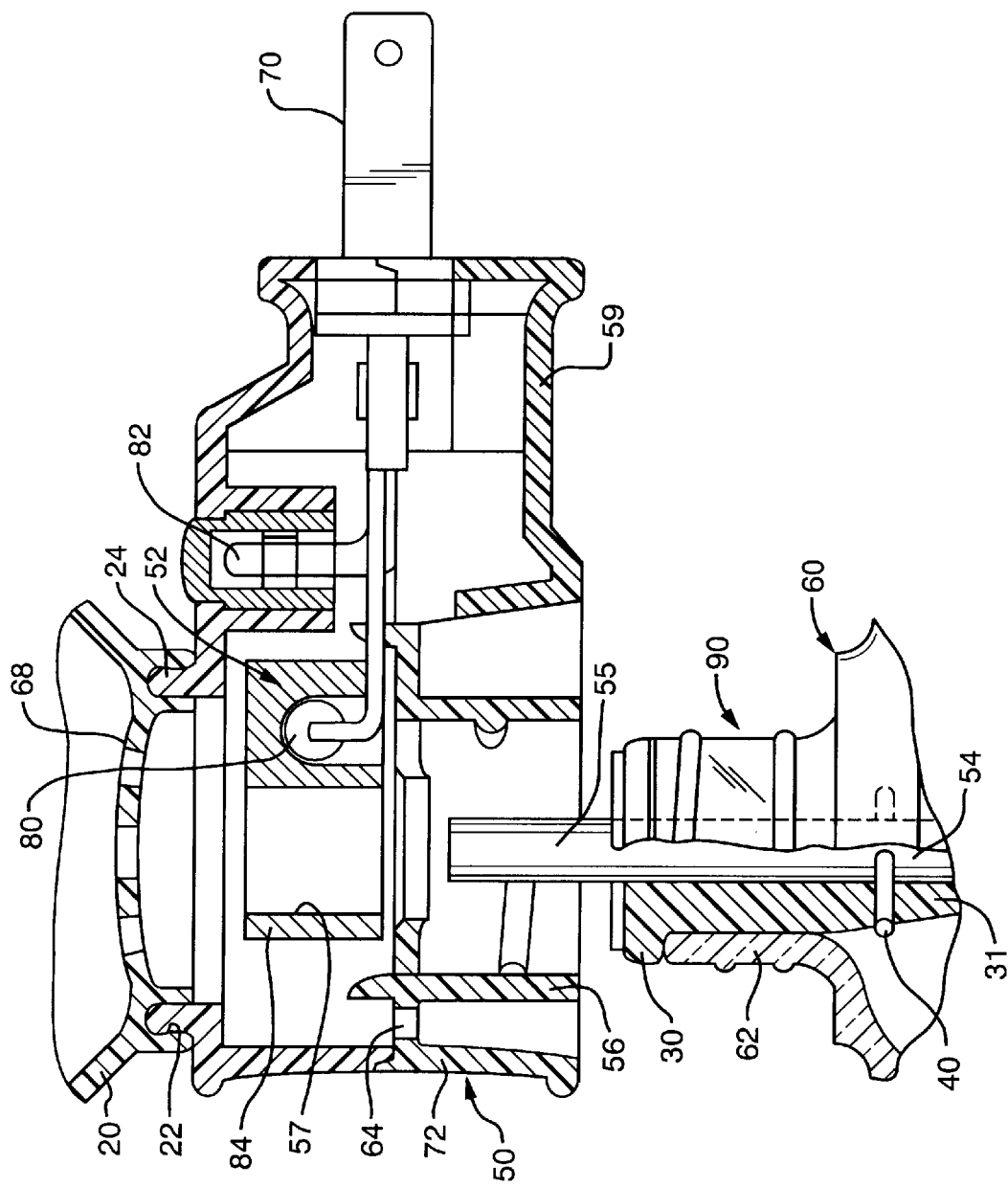
FIG. 4 is a sectional view of the system housing and part of the container of the present invention with an alternate form of the wick retaining ring.
Figure 6:
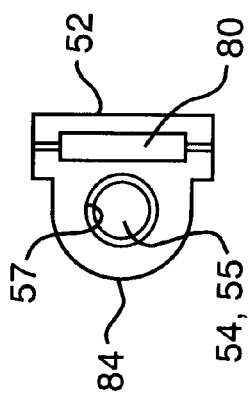
FIG. 6 is a top plan view of the heater assembly used in accordance with the present invention.

Referring to the drawings the miniaturized electric air freshener of the present invention is generally designated 10 in FIG. 2, and comprises a multi-part plastic vaporizer housing 50 containing a heater assembly 52 for heating the upper end of a wick 54 which is cylindrical in shape and has an upper end 55 that engages into a hole 57 extending through the heater assembly as shown in FIGS. 4 and 6. The vaporizer housing includes a reverse threaded socket 56 which receives the upper reverse threaded neck end of a bottle or container 60 that contains a liquid air freshening liquid shown at 62. Wick 54 absorbs the liquid and brings it to the upper end 55 by capillary action like a sponge, where it is heated and vaporized by the heater assembly 52.

The use of a reverse screw thread which is generally designated 90 in FIG. 4, means that container 60, when viewed from above, is turned clock-wise to tighten it onto the housing and counter-clock-wise to loosen and remove it, and that common forward screw thread bottles cannot be used in the system.

Socket 56 in the socket portion 51 of the housing 50, holds the bottle in place with all but the neck of the bottle extending below the housing and being exposed so that it can be seen.

The housing 50 includes a dome-shaped cover 68 having multiple holes in a pattern forming vapor outlets. The cover includes a decorative upwardly and outwardly extending flange 20 that mimics the leaves of a plant, the petals of a flower or other simulative shape. This shape helps conceal the dome, helps dissipate the evaporated air freshener and decorate the product as it rests near a wall, supported by a wall socket.

The device is energized by receiving electricity through a pair of electrical plug blades 70 which are meant to be plugged into an electric wall outlet. Blades 70 both supply electricity to, and support the product on the wall. Plug blades 70, and the generally rectangular plug portion 59 of the housing 50 are made as one unit. The plug is fixed with respect to the housing so that bottle 60 can only hang downwardly from the housing when the plug blades are plugged into the wall.

Housing 50, as best shown in FIG. 4, has a skirt 72 spaced around the socket 56 and the bottle neck 62 that would be in that socket, forming a clearance space which also contains air intakes 64.

Figure 3:
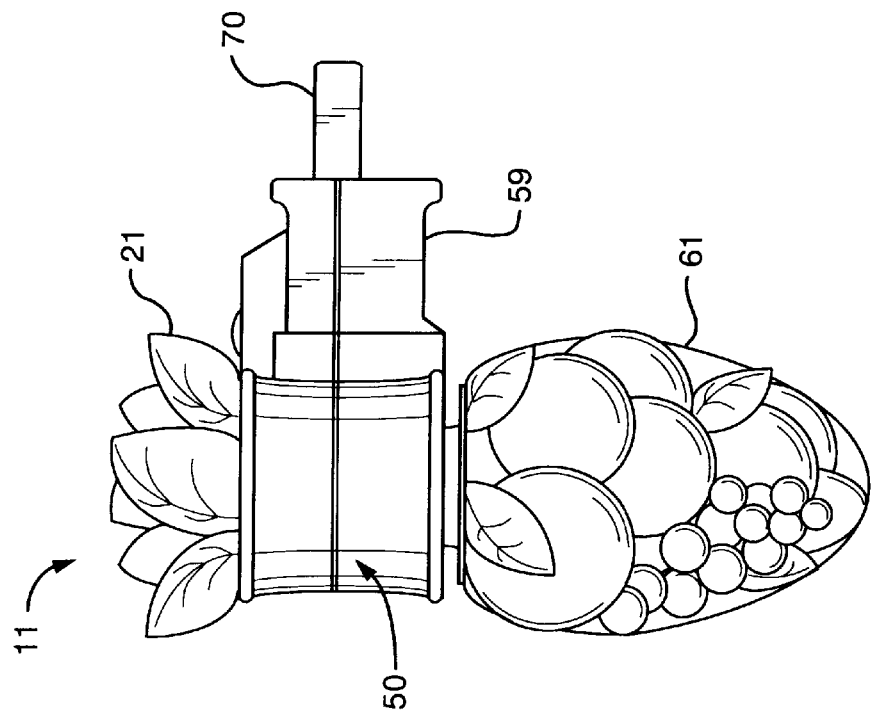
FIG. 3 is a view similar to FIG. 2 of another embodiment of the invention.

The design of the product is such to simulate fruits, vegetables, or other items. In FIG. 2 for example, housing 50 includes an upper cover flange 20 which simulates foliage around the outlet cover 68. The bottle itself may be shaped to simulate one fruit (e.g. FIG. 2) or a bunch of fruit 61 below the foliage 21 as shown in a device of the invention generally designated 11 in FIG. 3.

The product is miniaturized so that it conveniently hangs from the integral plug blades 70 and dispenses liquid fragrance as the fragrance is evaporated near the top of wick 54 by heat from the heater 52, the liquid being replenished by capillary action as more liquid is absorbed up from bottle 60 or 61 toward the top of wick 54.

Figure 1:
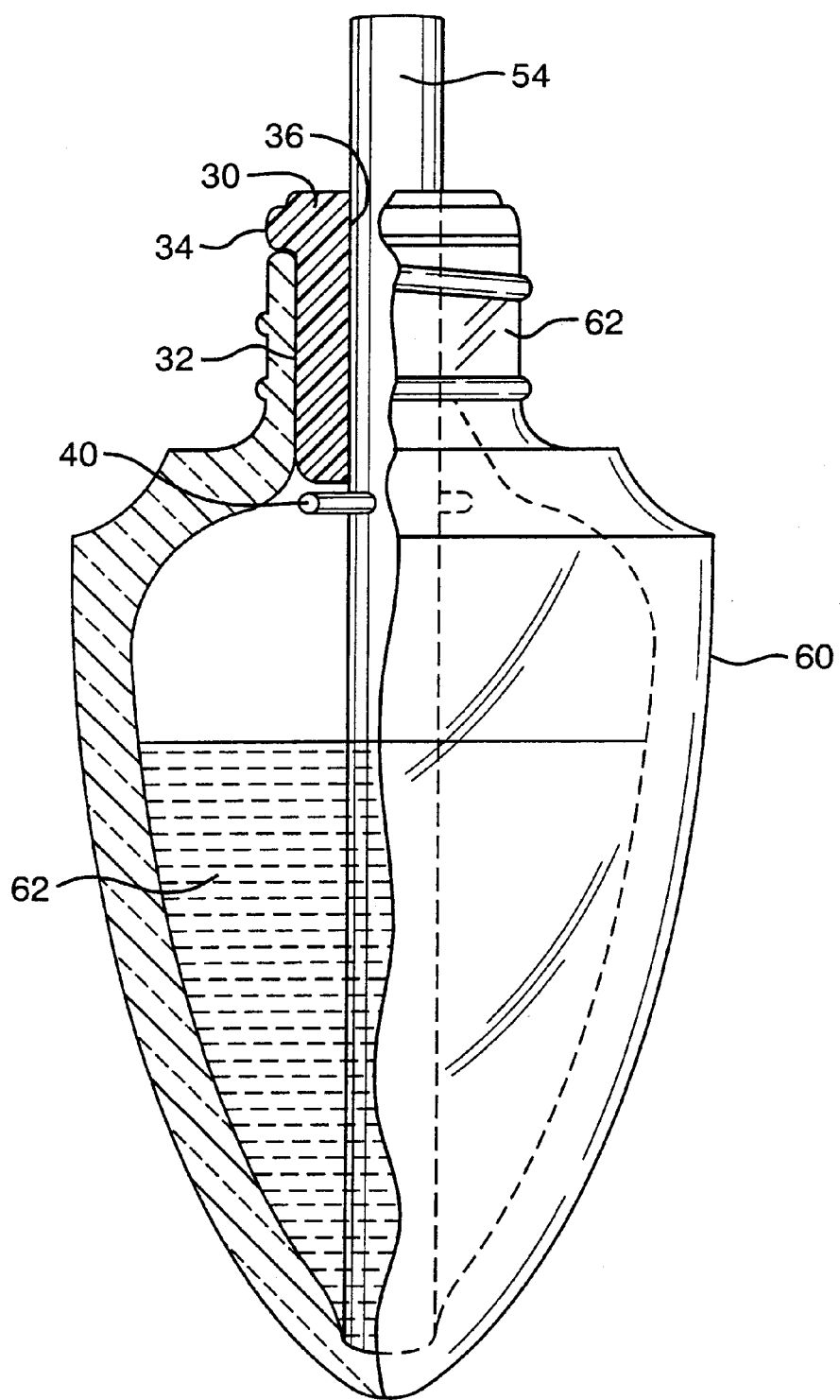
FIG. 1 is a side elevational view, partly in section, of a container for liquid to be evaporated in the system of the present inventions.

As best shown in FIG. 1, the child-resistant wick arrangement of the present invention includes a retaining ring 30 having a lower cylindrical portion 32 which closely engages by press fit and/or by use of adhesive, into neck 62 of bottle 60 so that it can not be removed. Advantageously, ring 30 is made of polypropylene or other high strength synthetic material such as nylon, and has an upper flange 34 forming the top of the bottle neck. A hole 36 extends through the center of ring 30 and has a diameter slightly less than the outer diameter of the flexible fibrous wick 54 so that the upper portion of the wick can extend through and be firmly held in hole 36 with the upper end of the wick extending above the neck so that it can be heated by the heater assembly. Wick 54 may be cotton, cellulose, polyester or other known wick material.

A steel pin 40 pierces through the fibrous wick 54 and is positioned just under retaining ring 30. Plastics or other sufficiently strong material may also be used for pin 40, which meet the required pull force. Pin 40 is long enough so that it extends radially beyond the periphery of wick 54 by an amount to preclude extraction of wick 54, upwardly through retaining ring 30. This, in conjunction with the permanent fixing of ring 30 to neck 62, prevents the extraction of the wick and thus exposure of children to the liquid 62 in the body portion of the bottle 60 and also prevents refilling.

The strength of pin 40 and the strength of the fit of retaining ring 30 in neck 62, which may be with or without adhesive, is such to require a pulling force of at least 15 pounds to extract wick 54 from the bottle. This effectively precludes extraction by a child and even is difficult for adults. As noted, this also makes it difficult to refill the container 60 with inappropriate liquids. In samples of the invention a force of over 15 pounds is needed to extract the wick as the pin is bent and the ring 30 is pulled from the neck.

FIG. 4 illustrates an alternate form of ring 30 which includes a cylindrical extension, skirt or sleeve 31 that encircles the wick and through which the pin 40 extends for added strength and resistance to removal of the wick.

Further, the polypropylene retaining ring 30 may have a portion 32 which is slightly greater in diameter than the inner passage through neck 62 so that a firm force is required to push ring 30 into the neck. This simultaneously contracts portion 32 of the neck and, with wick 54 in place, effectively squeezes the wick even more firmly within the hole 36. At the same time, the force fit is achieved, preferably without adhesive.

Figure 5:
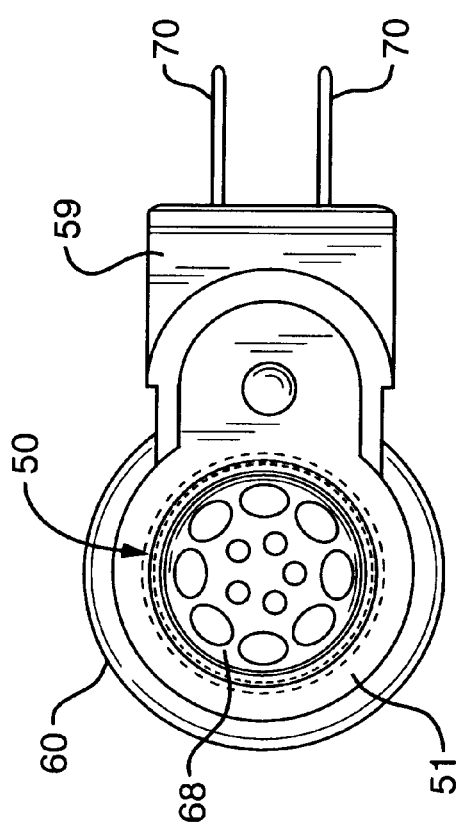
FIG. 5 is a top plan view of the system with the flange removed to reveal underlying structures.

To advance the decorative aspects of the invention, as shown in FIG. 5, the largest diameter of the bottle body is selected to be larger than the diameter of a socket portion 51 of the housing 50. Socket portion 51 is connected to the plug portion 59. Socket portion 51 contains socket 56 and is so named for that purpose, while plug portion 58 carries the plug blades 70 and internal wiring which extend to a tangential, substantially straight electric heater 80 and an optional LED 82 which is lit by electricity to indicate that the system has been powered and is evolving vapor from the cover 68.

As shown in FIG. 6 and as fully disclosed in U.S. Pat. No. 5,222,186, tangential heater assembly 52 comprises the tangential heater 80 which is surrounded by a ceramic potting material body 84. As shown in FIG. 4, heater 80 sits in one recess in the body 84 and body 84 also contains the passage or opening 57 for receiving the upper end 55 of wick 54. Opening 57 may be slightly larger than the outer diameter of wick 55 to allow easy insertion of a new wick when the liquid in a container 60 has been depleted, the upper end 55 of wick 54 being automatically inserted to opening 57 when neck 62 is threaded into socket 56.

FIG. 4 also illustrates the one piece construction of cover 68 which includes the decorative and functional flange 20. An annular groove 22 at the base of the cover receives and snap fits to an annular rim 24 extending upwardly from the housing 50. This allows the decorative flange 20 in FIG. 2 or 21 in FIG. 3, to be snap fit onto the housing and perhaps even to be replaced with different decorations that are consistent with the decoration on the bottle 60 or 61.

In FIG. 1, bottle 60 is advantageously made of glass. Any material which is compatible with the liquid, in particular air freshening liquid, to be evaporated from the unit, can be used as the container.

While specific embodiments of the invention have been shown and described in detail to illustrate the application of the principles of the invention, it will be understood that the invention may be embodied otherwise without departing from such principles.

What is claimed is:

1. A vapor emanation system comprising:
   a housing having a socket portion;
   a container for containing liquid to be evaporated by heat, the container having a body for storing the liquid and a neck connected to the body and for engaging the socket portion of the housing for supporting the container on the housing, the neck having a passage there through;
   a retaining ring fixed in the passage and having a hole there through;
   a wick having an upper portion extending through the hole of the retaining ring, and a lower portion extending down into the body of the container for absorbing liquid from the container and for moving the liquid into the upper portion of the wick by capillary action;
   heating means in the housing for heating the upper portion of the wick above the neck to evaporate liquid from the wick; and
   a retaining pin extending through the wick below the neck, the retaining pin extending beyond the wick by an amount which precludes upward extraction of the wick from the retaining ring.

2. A system according to claim 1, wherein the pin is metal and the retaining ring is press fit into the neck.

3. A system according to claim 1, wherein the pin extends radially through the wick below the retaining ring and is longer in length than a diameter of the hole of the retaining ring.

4. A system according to claim 1, wherein the container has a decorative body which simulates an item and is visible below the housing.

5. A system according to claim 4, including a flange extending upwardly from the housing and simulating a further item which is consistent with the item simulated by the bottle body.

6. A system according to claim 1, wherein the container and the socket portion are connected to each other by reverse screw threads.

7. A system according to claim 1 wherein the socket portion has a diameter, the housing including a plug portion, the neck being removably threaded to the socket portion of the housing for supporting the container on the housing, the neck having a passage there through and the body having a maximum diameter that is larger than the diameter of the socket portion of the housing, the body extending downwardly from the housing with no part of the housing covering the body so that the body is visible below the housing and electric blade means connected to the heating means and supported by the plug portion of the housing for being plugged into an electric wall socket for powering the heating means and for supporting the system on the wall.

8. A vapor emanation system comprising:
   a housing having a socket portion with a diameter and a plug portion connected to the socket portion;
   a container for containing liquid to be evaporated by heat, the container having a body for storing the liquid and a neck removably threaded to the socket portion of the housing for supporting the container on the housing, the neck having a passage there through and the body having a maximum diameter that is larger than said diameter of the socket portion of the housing, the body extending downwardly from the housing with no part of the housing covering the body so that the entire body is visible below the housing;
   a wick having an upper portion extending through the passage of the neck, and a lower portion extending down into the body of the container for absorbing liquid from the container and for moving the liquid into the upper portion of the wick by capillary action;
   heating means in the housing for heating the upper portion of the wick above the neck to evaporate liquid from the wick; and
   electric blade means connected to the heating means and supported by the plug portion of the housing for being plugged into an electric wall socket for powering the heating means and for supporting the system on the wall.

9. A system according to claim 8, including a retaining ring fixed in the passage of the neck and having a hole there through, the wick extending through the hole of the retaining ring and a retaining pin extending through the wick below the neck, the retaining pin extending beyond the wick by an amount which precludes upward extraction of the wick from the retaining ring.

10. A system according to claim 9, wherein the pin is metal and the retaining ring is press fit into the neck.

11. A system according to claim 9, wherein the pin extends radially through the wick below the retaining ring and is longer in length than a diameter of the hole of the retaining ring.

12. A system according to claim 8, wherein the container has a decorative body which simulates an item and is visible below the housing.

13. A system according to claim 12, including a flange extending upwardly from the housing and simulating a further item which is consistent with the item simulated by the bottle body.

14. A system according to claim 8, wherein the heating means is a tangential heater in the socket portion of the housing.

15. A system according to claim 13, wherein the flange includes a perforated dome and an annular recess, the socket portion of the housing including a rim for engagement by the annular recess to hold the dome and flange to the housing.

16. A system according to claim 8, wherein the neck and socket portion have reverse screw threads for engaging each other.

17. A vapor emanation system comprising:

a housing having a socket portion containing a reverse female thread, and a plug portion;

a container for containing liquid to be evaporated by heat, the contained having a body for storing the liquid and a neck with a reverse male thread, the neck being removably threaded to the socket portion of the housing for supporting the contained on the housing, the body extending downwardly from the housing;

a wick having an upper portion extending through the passage of the neck, and a lower portion extending down into the body of the contained for absorbing liquid from the contained and for moving the liquid into the upper portion of the wick by capillary action;

heating means in the housing for heating the upper portion of the wick above the neck to evaporate liquid from the wick;

electric blade means connected to the heating means and supported by the plug portion of the housing for being plugged into an electric wall socket for powering the heating means and for supporting the system on the wall; and a retaining ring fixed in the passage of the neck and having a hole there through, the wick extending through the hole of the retaining ring and a retaining pin extending through the wick below the neck, the retaining pin extending beyond the wick by an amount which precludes upward extraction of the wick from the retaining ring.

18. A system according to claim 17, wherein the pin is metal and the retaining ring is press fit into the neck.

19. A vapor emanation system comprising:

a housing having a socket portion containing a reverse female thread, and a plug portion;

a container for containing liquid to be evaporated by heat, the contained having a body for storing the liquid and a neck with a reverse male thread, the neck being removably threaded to the socket portion of the housing for supporting the contained on the housing, the body extending downwardly from the housing;

a wick having an upper portion extending through the passage of the neck, and a lower portion extending down into the body of the contained for absorbing liquid from the contained and for moving the liquid into the upper portion of the wick by capillary action;

heating means in the housing for heating the upper portion of the wick above the neck to evaporate liquid from the wick;

electric blade means connected to the heating means and supported by the plug portion of the housing for being plugged into an electric wall socket for powering the heating means and for supporting the system on the wall; and a pin extending radially through the wick below a retaining ring for the wick, the pin being longer in length than a diameter of the hole of the retaining ring for the wick.

* * * * *